United States Patent
Yi et al.

(10) Patent No.: US 9,153,114 B2
(45) Date of Patent: Oct. 6, 2015

(54) FALL DETECTION METHOD AND SYSTEM

(71) Applicants: Ge Yi, San Ramon, CA (US); Dujiang Wan, Fremont, CA (US)

(72) Inventors: Ge Yi, San Ramon, CA (US); Dujiang Wan, Fremont, CA (US)

( * ) Notice: Subject to any disclaimer, the term of this patent is extended or adjusted under 35 U.S.C. 154(b) by 71 days.

(21) Appl. No.: 14/174,847

(22) Filed: Feb. 7, 2014

(65) Prior Publication Data

US 2015/0228177 A1 Aug. 13, 2015

(51) Int. Cl.
*G08B 21/00* (2006.01)
*G08B 21/04* (2006.01)
*G01P 15/08* (2006.01)
*G08B 13/10* (2006.01)
*G01P 15/03* (2006.01)

(52) U.S. Cl.
CPC .......... *G08B 21/0446* (2013.01); *G01P 15/036* (2013.01); *G01P 15/08* (2013.01); *G08B 13/10* (2013.01)

(58) Field of Classification Search
CPC .......... G01P 15/06; G01P 15/00; G01P 3/22; G01P 15/08; G01P 15/036; G08B 21/0446
USPC ........ 340/665, 539.13, 539.22, 669; 600/595; 360/75; 73/510; 702/141; 116/203, 116/200, 205
See application file for complete search history.

(56) References Cited

U.S. PATENT DOCUMENTS

| | | | | |
|---|---|---|---|---|
| 4,091,250 A * | 5/1978 | Siiberg | | 200/84 C |
| 6,681,627 B1 * | 1/2004 | Li | | 73/307 |
| 7,150,048 B2 * | 12/2006 | Buckman | | 2/465 |
| 8,628,453 B2 * | 1/2014 | Balakrishnan et al. | | 482/1 |
| 8,909,497 B1 * | 12/2014 | Shkolnikov | | 702/141 |
| 8,921,115 B2 * | 12/2014 | Yuan et al. | | 436/69 |
| 2002/0166756 A1 * | 11/2002 | Thompson | | 200/61.52 |
| 2005/0027216 A1 * | 2/2005 | Guillemaud et al. | | 600/595 |
| 2005/0235385 A1 * | 10/2005 | Wehrenberg | | D14/125 |
| 2005/0242947 A1 * | 11/2005 | Burneske et al. | | 340/539.13 |
| 2006/0001545 A1 * | 1/2006 | Wolf | | 340/573.1 |
| 2006/0236761 A1 * | 10/2006 | Inoue et al. | | 73/510 |
| 2006/0279426 A1 * | 12/2006 | Bonnet et al. | | 340/573.1 |
| 2007/0030587 A1 * | 2/2007 | Noda et al. | | 360/75 |
| 2008/0214963 A1 * | 9/2008 | Guillemaud et al. | | 600/595 |
| 2010/0010771 A1 * | 1/2010 | Ikkink et al. | | 702/141 |
| 2010/0253530 A1 * | 10/2010 | Pan et al. | | 340/665 |
| 2010/0283618 A1 * | 11/2010 | Wolfe et al. | | 340/575 |
| 2011/0152727 A1 * | 6/2011 | Ten Kate | | 600/595 |
| 2011/0201972 A1 * | 8/2011 | Ten Kate | | 600/595 |
| 2012/0016270 A1 * | 1/2012 | Buhler et al. | | 600/595 |
| 2012/0095722 A1 * | 4/2012 | Ten Kate | | 702/141 |
| 2012/0101411 A1 * | 4/2012 | Hausdorff et al. | | 600/595 |
| 2012/0191405 A1 * | 7/2012 | Molyneux et al. | | 702/141 |
| 2013/0054180 A1 * | 2/2013 | Barfield | | 702/138 |
| 2013/0120147 A1 * | 5/2013 | Narasimhan et al. | | 340/573.1 |
| 2014/0191863 A1 * | 7/2014 | Ten Kate | | 340/539.12 |
| 2014/0276239 A1 * | 9/2014 | Subramaniam et al. | | 600/595 |

* cited by examiner

*Primary Examiner* — Hoi Lau

(57) ABSTRACT

Fall detection method and systems with its unique designed sensors are disclosed. The capacitive sensing based systems use the abrupt changes of the capacitance value to detect whether a real fall event happens, while the reed sensor/or reed switch based systems work in power saving passive mode to detect the real fall event by analyzing the binary "on/off" signal available from the reed sensor/or reed switch. Both rely on the orientation change of the host body respects to local gravity direction during the falling process. The system can present either as a standalone system or a built-in component with supporting software installed on other devices.

18 Claims, 15 Drawing Sheets

FALL DETECTION METHOD AND SYSTEM

RELATED APPLICATIONS

The present application claims of the priority benefit of U.S. patent application Ser. No. 29/469,035 filed on Oct. 7, 2013 as Design application and U.S. patent application Ser. No. 14/161,695 filed on Jan. 23, 2014 as Utility application entitled "UNIVERSAL FALL DETECTION SYSTEM," which is incorporated herein by reference.

FIELD OF INVENTION

Universal fall detection and response system, and more particularly, using sensor system to detect the fall of host based on relative position/orientation between host body and direction of gravity at the spot where a falling event happens was disclosed in U.S. patent application Ser. No. 29/469,035 and Ser. No. 14/161,695.

This disclosure is related to falling detection method and detection system design as well as more alternative falling sensor designs.

BACKGROUND ART

Fall detection is very important and has widely applications in older care, patient care, child care, disable care as well as safety for outdoor sports, such as ski, mount bike, hiking, cycling. To develop a reliable fall detection system has huge market potential and great society impact.

Conventional fall detection system is designed to detect whether a real fall event happens by matching falling acceleration data with pre-set models or thresholds using enormous different kinds of algorithm. However, a random fall event depends on actual situation and prior falling movement of the host. It is so complicated that it is almost impossible to have a precise model to mimic the real events for each particular case. Despite of great efforts, there is no a successful product existing on the market with great impact. In U.S. patent application Ser. No. 29/469,035 and Ser. No. 14/161,695, a universal fall detection system and different falling sensor designs are disclosed to resolve this dilemma by directly measuring/sensing the relative position/orientation between the host body and direction of gravity at the spot where a falling event happens.

In this disclosure, our unique detection methodology and detection system design as well as more alternative falling sensor designs are disclosed.

As used herein, the term "or" may be construed in either an inclusive or exclusive sense. Similarly, the term "exemplary" is construed merely to mean an example of something or an exemplar and not necessarily a preferred or ideal means of accomplishing a goal. Additionally, although various exemplary embodiments discussed below focus on quality control of professionals, the embodiments are given merely for clarity and disclosure. Alternative embodiments may employ other systems and methods and are considered as being within the scope of the present invention.

SUMMARY OF THE INVENTION

A universal fall detection system in form of, either an independent portable device or built-in component in smart phone, or tablet, or other portable device such as Google glass, etc., is disclosed in U.S. patent application Ser. Nos. 29/469,035 and Ser. No. 14/161,695. The core of the system is a sensor subsystem, which senses the relative orientation/position of the host body with the direction of the gravity at the spot to detect whether a falling event happens using a floating object, whose gravity is well balanced by force provided by other component(s) within sensor subsystem before fall. The capability of sensing breakage of the balance and move away from its equilibrium position due to fall event gives new class of fall detection system design.

Several alternative designs of sensor sub-system as well as the associated electronic block arrangements are disclosed in this patent application. The detailed sensing signal patterns are disclosed as the core for our unique detection method. Several proposed signal processing methods are addressed in this patent application. The system can be integrated as a miniature system-on-chip device, which is capable of low cost large volume manufacture.

BRIEF DESCRIPTION OF THE DRAWINGS

Various ones of the appended drawings merely illustrate exemplary embodiments of the present invention and cannot be considered as limiting its scope.

DETAILED DESCRIPTION

The following description is provided in the context of particular designs, applications and the details, to enable any person skilled in the art to make and use the invention. However, for those skilled in the art, it is apparent that various modifications to the embodiments shown can be practiced with the generic principles defined here, and without departing the spirit and scope of this invention. Thus, the present invention is not intended to be limited to the embodiments shown, but is to be accorded the widest scope consistent with the principles, features and teachings disclosed here. In general, well-known instruction instances, protocols, structures and techniques have not been shown in detail.

Figure 1:
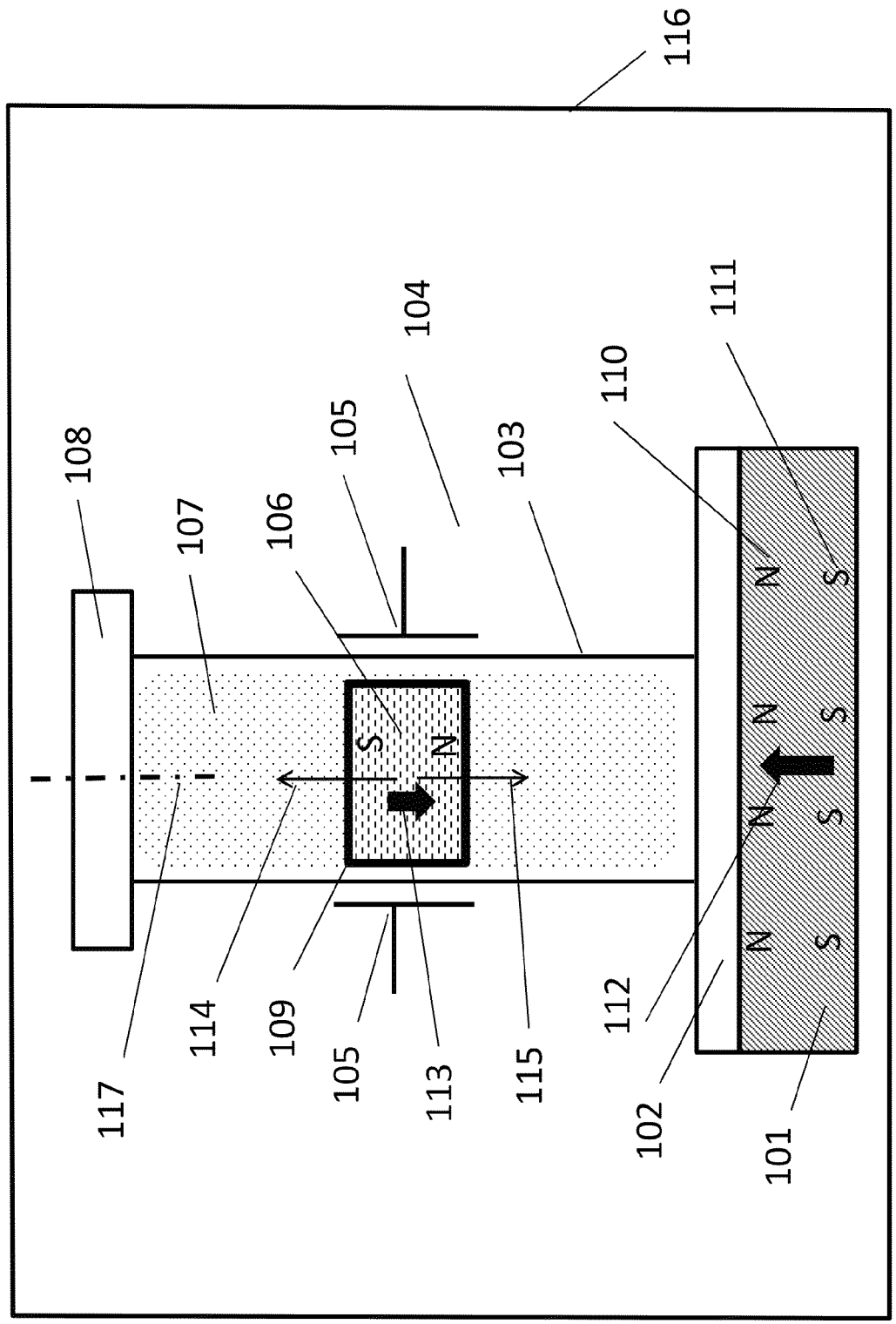
FIG. 1 illustrates one of the sensor embodiments based on capacitive sensing for detecting relative orientation change between the host body and direction of gravity.
Figure 6:
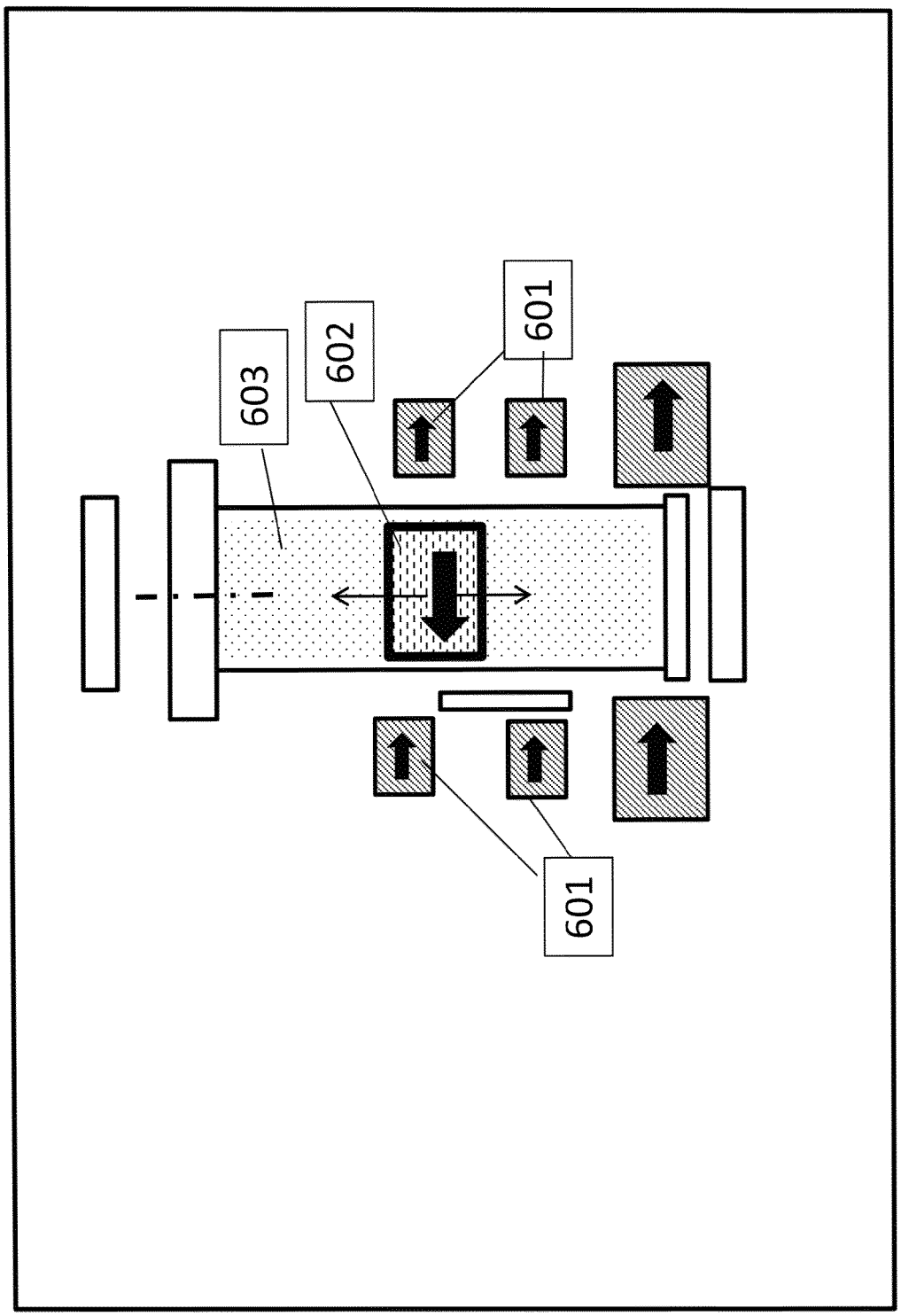
FIG. 6 illustrates one of the embodiments similar to FIG. 5 but with more magnets for reducing the contact between the floating magnet and side wall.

FIG. 1 illustrates one of the sensor embodiments based on capacitive sensing for detecting relative orientation change between the host body and direction of gravity, which is the same as that shown in FIG. 6 in U.S. patent application Ser. No. 29/469,035 and Ser. No. 14/161,695. The sensor comprises a bottom permanent magnet 101 (e.g. either a continue magnetic film or patterned magnet); an optional non-magnetic space layer 102; a free space in form of tube 103 made within the dielectric matrix 104; a small permanent magnet 106 floating inside tube 103 with coating layer 109 for reducing the friction between the magnet 106 and side wall of tube 103; a lid 108 on top of the tube 103 to prevent the magnet 106 from moving out of the tube 103 when fall happens; and a pair of electrodes 105, which forms a capacitive sensor and locates in the equilibrium position of magnet 106.

As shown in FIG. 1, the permanent magnet (or magnetic layer) 101 has its magnetization 112 pointing up with north magnetic pole 110 on the top surface and south magnetic pole 111 at the bottom surface, while, on the other hand, the small magnet 106 has its magnetization 113 pointing down with its north magnetic pole at its bottom and south magnetic pole on top. The magnetostatic repelling force 114 on magnet 106 from the permanent magnet 101 provides the magnet 106 supporting to float inside tube 103 before falling against the gravity 115 of the magnet 106 shown in FIG. 1 when the center line 117 of tube 103 parallel to direction of local gravity 115. The capacitance between the pair of electrodes 105 is proportional to EA/d, while A is the facing area of the two electrodes 105, d is the distance of the two electrodes, and c is permittivity of material between the electrodes. Any tilting of the center line 117 away from the vertical direction due to fall will drive the magnet 106 away from its vertical equilibrium position, resulting in the capacitance change between the pair of electrodes 105 due to the change of permittivity ∈. The capacitance sensor can be used to sense a falling event by detecting the directional change of the gravity 117 respect to the center line 117.

The medium 107 filled inside the tube 103 can be air, a kind of gas, a kind of liquid, or even vacuum. A soft magnetic shield 116 can be built around the sensor in order to eliminate interference or disturbing from any external magnetic field. Multiple pairs of sensor pairs can be made along the tube 103 to precisely sense the magnet 106 moving during the fall, and thus define and characterize the fall.

Figure 2:
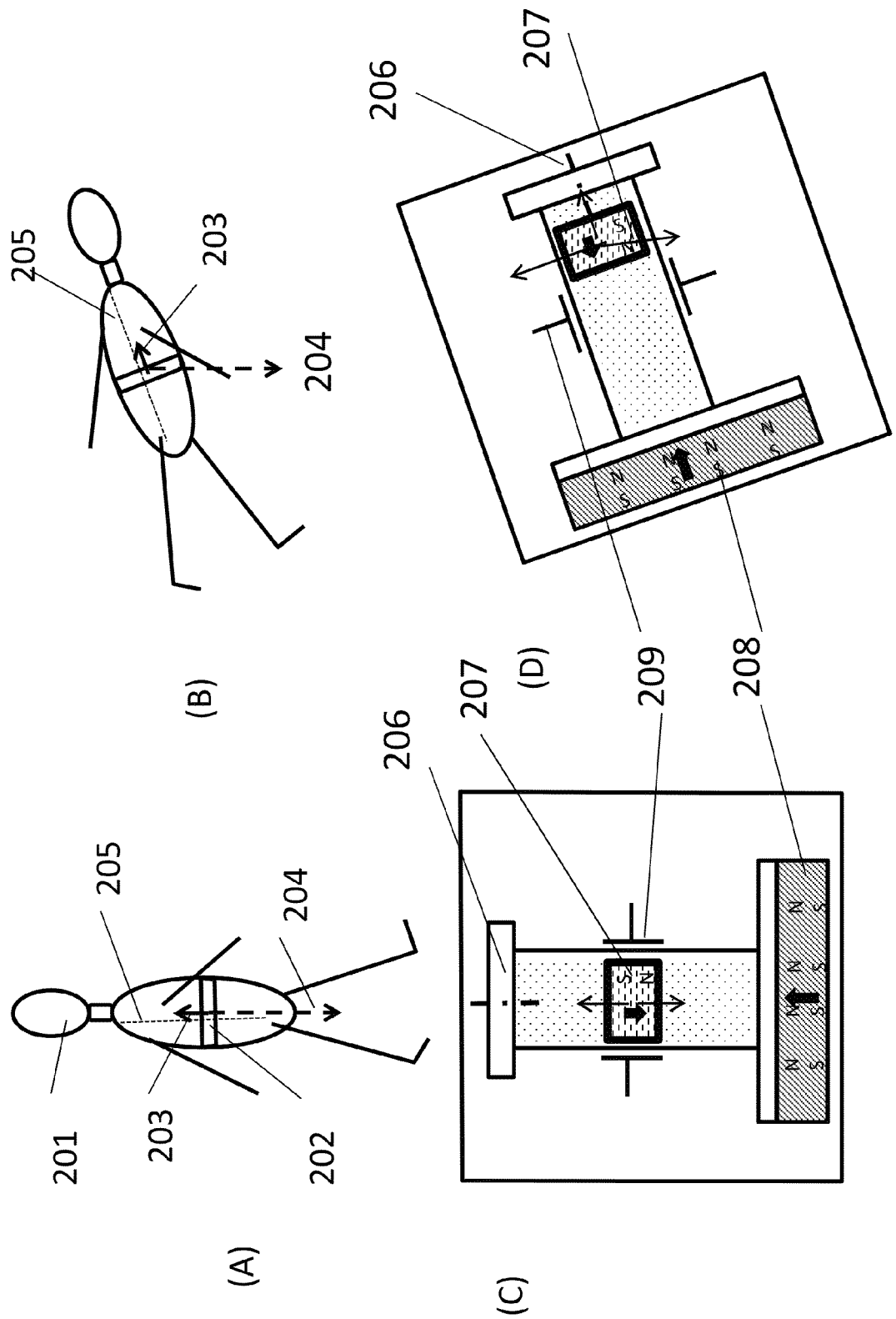
FIG. 2A-2D show the detection mechanism of the proposed fall detection system by sensing the relative position or orientation of host body with the direction of gravity at the event of fall.

FIG. 2A-2D illustrate the fall detection mechanism of the proposed sensor design in FIG. 1 when the host falls. The host 201 can be anything such as a human, a robot, or a vehicle, whose fall is our major concern. The host's body center-line 203 can be used as a general reference for the host's body orientation. In the particular scenario described here, the host 201 is a human, whose spine 205 is used as a reference for the center-line 203 of the human body. FIG. 2A and FIG. 2B describe the situations before and after fall happens, while FIG. 2C and FIG. 2D show the sensor's orientation change before and after fall happens. In order to make the sensor works, the central line 206 (shown in FIG. 1 as 117) of the sensor 202 always aligns with the body centerline 203 of the host 201, which are all parallel with the repelling force direction between the floating magnet 207 and bottom magnet 208.

Regardless of the details of how the fall happens and the details of the speed or the acceleration before and after fall, the angle between the host body center-line 203 and local gravity 204 has quite noticeable change. It would be extremely reliable for the fall detection system to only sense the angle change caused by the fall event. The fall event drives the floating magnet 207 (shown in FIG. 1 as 106) away from its equilibrium position in FIG. 2C that result in the capacitance change of the capacitive sensor 209. The capacitance change picked up by sensor electronics is a perfect signal for fall detection.

Figure 3:
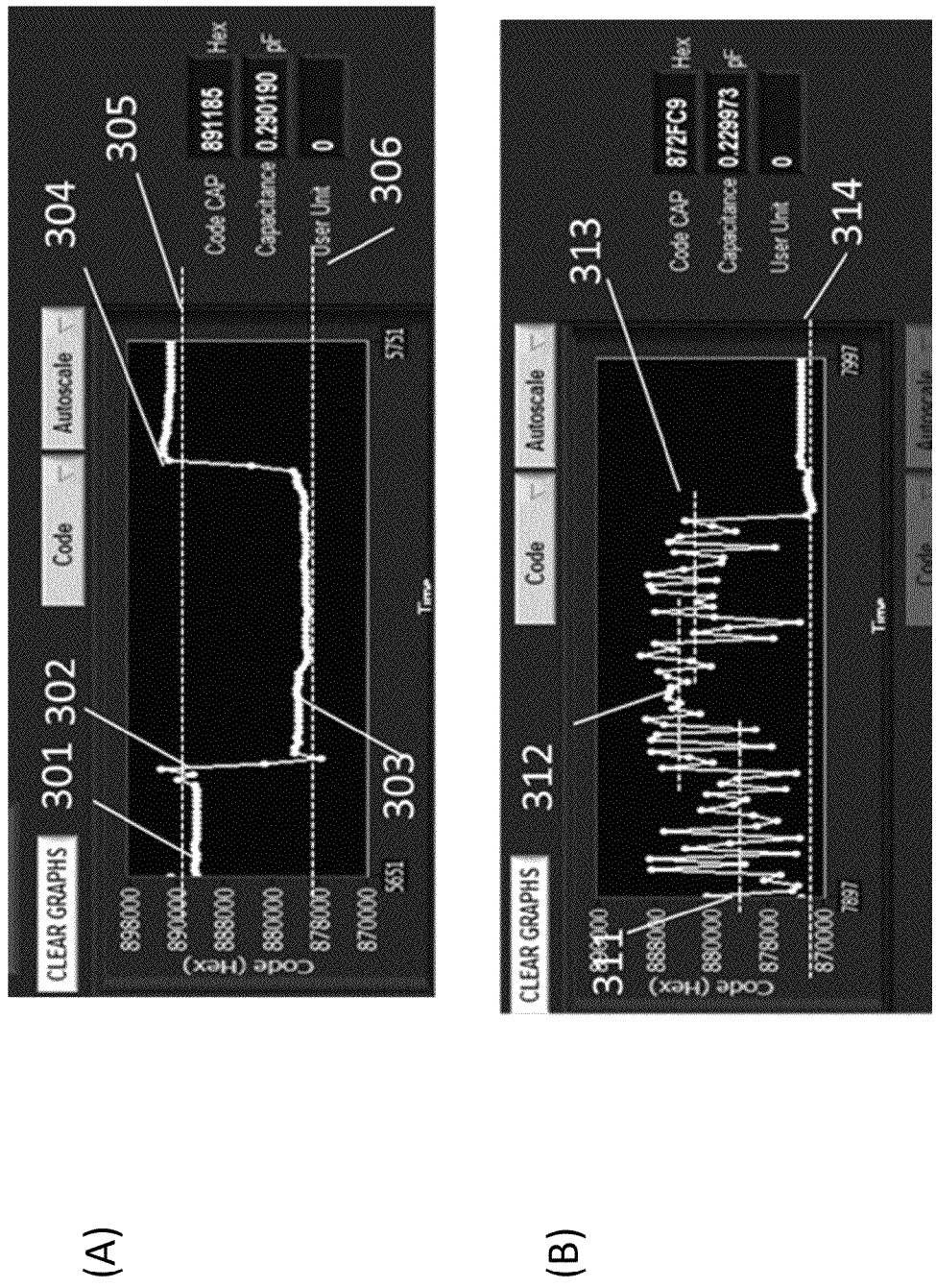
FIG. 3A-3B show two exemplary capacitance changes during falling from a demonstration system, in which the dropping (or rising) of the capacitance value.

FIG. 3A-3B show two exemplary capacitance change signals during falling from a demonstration system. The dropping (or rising) of the capacitance value is detected by the sensor (shown in FIG. 1) who is connected to capacitance-digital-convertor (CDC). In FIGS. 3A-3B, Y and X axes are the digitized capacitance value output from the sensor system and time, respectively. For this particular sensor-CDC connection, the high capacitance value corresponds to the body position of the host before fall. This can be changed depends on the connection between sensor to sensor-monitoring circuit or electronics.

FIG. 3A shows one exemplary evolution of sensor capacitance signal against time, which corresponds to a sequence of events for the host: normal standing position—fall on the ground due to tripping—recover and standup again. The capacitance values of dot-lines 305 and 306 in FIG. 3A represent the host body's two static statuses, i.e., standing straight and lying on the ground, respectively. Starting from signal 301 normal host's standup status, the sensor capacitance change signal from 302 to 303 indicates that the host was triggered to fall down by some events. Signal 303 represents the host's fall down status. The sensor capacitance change signal from 303 to 304 indicates the host's recovery from the fall status to full standup again. The sudden change of capacitance (in this case—a drop) at 302 is a characteristic feature for our novel fall detection method. As stated previously, depending on wiring between the sensor and detection electronics, the change can be a sudden jump of the capacitance value. In the real system, more sophistic algorithms such as differential signal processing and smoothing, can be implemented, which will be covered in separated disclosure. The raw capacitance value is continually monitored and recorded in order to track the host's fall recovery after host's fall.

FIG. 3B is another example of the capacitance value change recorded to simulate the case of fall detection during ski. The different capacitance values of signal 311, 312 and 313 correspond to different host body's tilting angles respect to local gravity during skiing. The dot-line 314 is the sensor's capacitance value when host body lies on the ground. The large variations of capacitance signal output indicate the high sensitivity of the sensor system to floating magnet dynamic movement in the sensor (FIG. 1 106) induced by the large host's acceleration. With more refined algorithm, the proposed system can be easily adopted to use for outdoor sport event monitoring fall and fall recovery and ensure better safety for the host.

Figure 4:
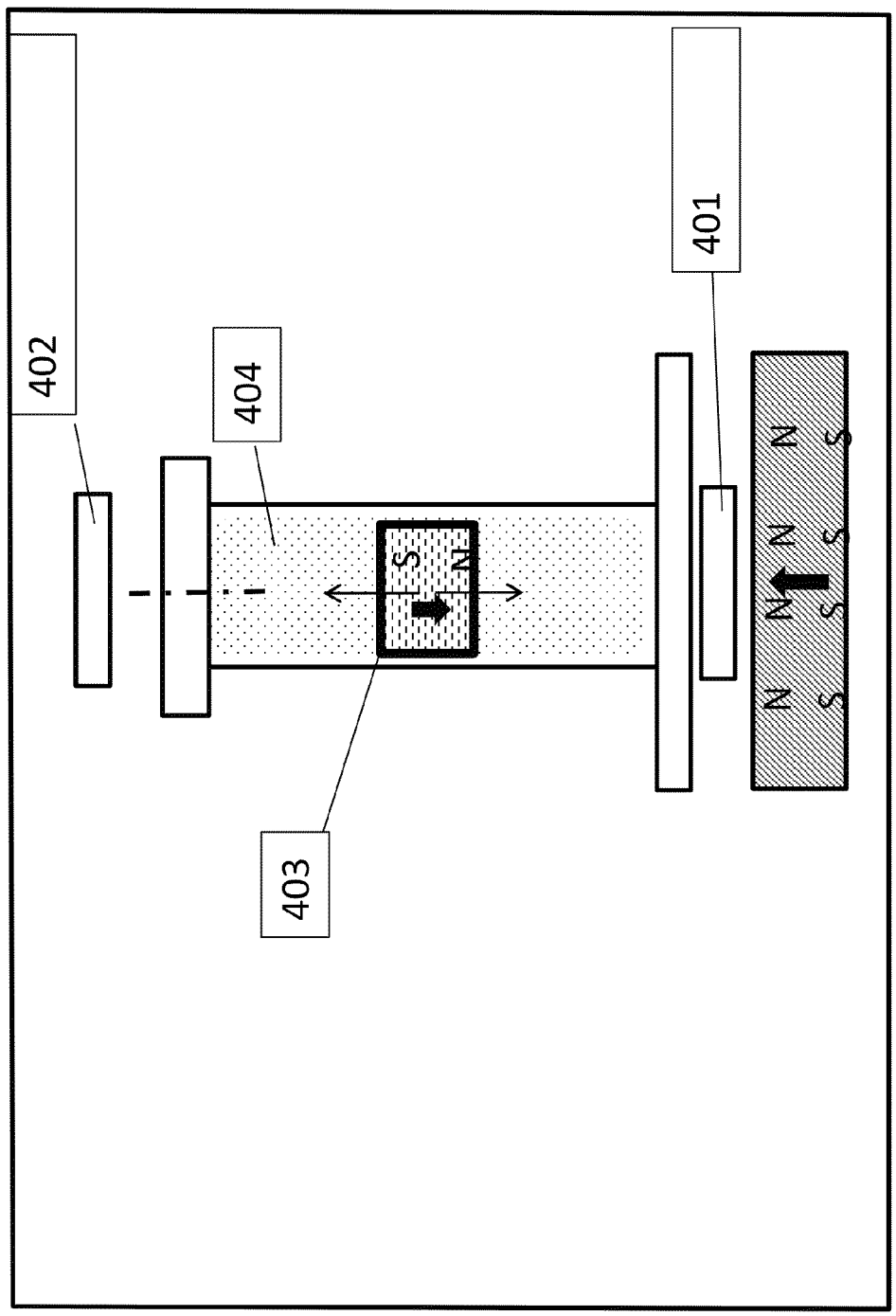
FIG. 4 illustrates another embodiment for capacitive signal based falling sensor similar that shown in FIG. 1.

FIG. 4 illustrates another embodiment of the proposed sensor design. Compared with the sensor shown in FIG. 1, while maintaining the most components as the same as that in FIG. 1 with the same principle for floating magnet 403 based on magnetic levitation, the capacitance sensor location has changed in FIG. 4. Instead of using capacitive sensor 105 as shown in FIG. 1, capacitive sensor 401 or 402 is now locating either below or above the hollow tube 404. Although there are two capacitive sensors 401 and 402 shown in FIG. 4, only one is needed to make the sensor work. The exact trace design of capacitive sensor for sensor 401 and sensor 402 can be altered and depends on the processes for making the sensor. As an example, a standard so-called capacitive button sensor is sufficient enough for serving the purpose.

Figure 5:
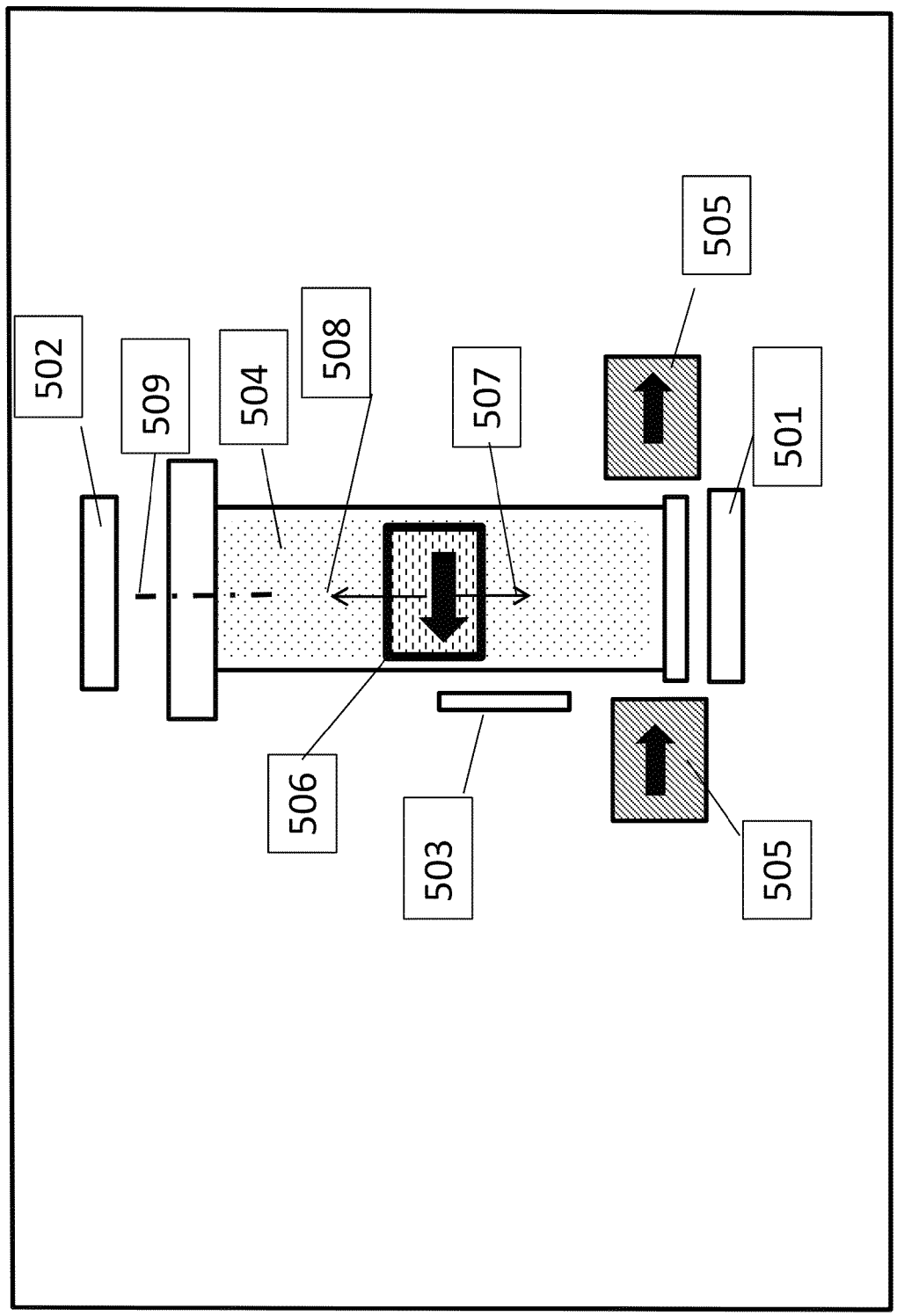
FIG. 5 illustrates alternative arrangement of the magnetization direction on another embodiment for capacitive signal based falling sensor.

FIG. 5 shows another embodiment of the proposed sensor design. Compared with the sensor shown in FIG. 4, it is noticeable that the magnetization of the floating magnet 506 and bottom magnet 505 are horizontal instead of vertical. Despite of the change of magnetization orientation, the direction of the magnetization in floating magnet 506 is opposite to the one in 505 so that the magnetic repelling force 508 from the 505 on floating magnet 506 will balance with its gravity 507 to maintain the magnetic levitation of 506. Any one of capacitive sensor, shown here as 501, 502, and 503, can be used again for sensing the location of the floating magnet 506 against it equilibrium location. Whenever the sensor centerline 509 is tilting away from the local gravity direction, the location of the 506 within the tube 504 will change thus the relative position between the capacitive sensor and floating magnet 506, which induces the change of capacitance output value from the sensor. The exact location of the bottom magnet 505 can change depends on detailed design as long as the principle of magnetic levitation holds.

FIG. 6 illustrates another embodiment of sensor design, which is very much similar to the one shown in FIG. 5, while there are extra pairs of the magnets 601 outside the hollow tube 603. The purpose of the extra pair of magnets, with opposite magnetization as floating magnet 602 is to push 602 away from the inner wall of the hollow tube 603 to reduce the friction force between 602 and 603 to ensure smooth movement of the floating magnet 602. The exact arrangement and the number of pairs of magnet can be changed.

Figure 7:
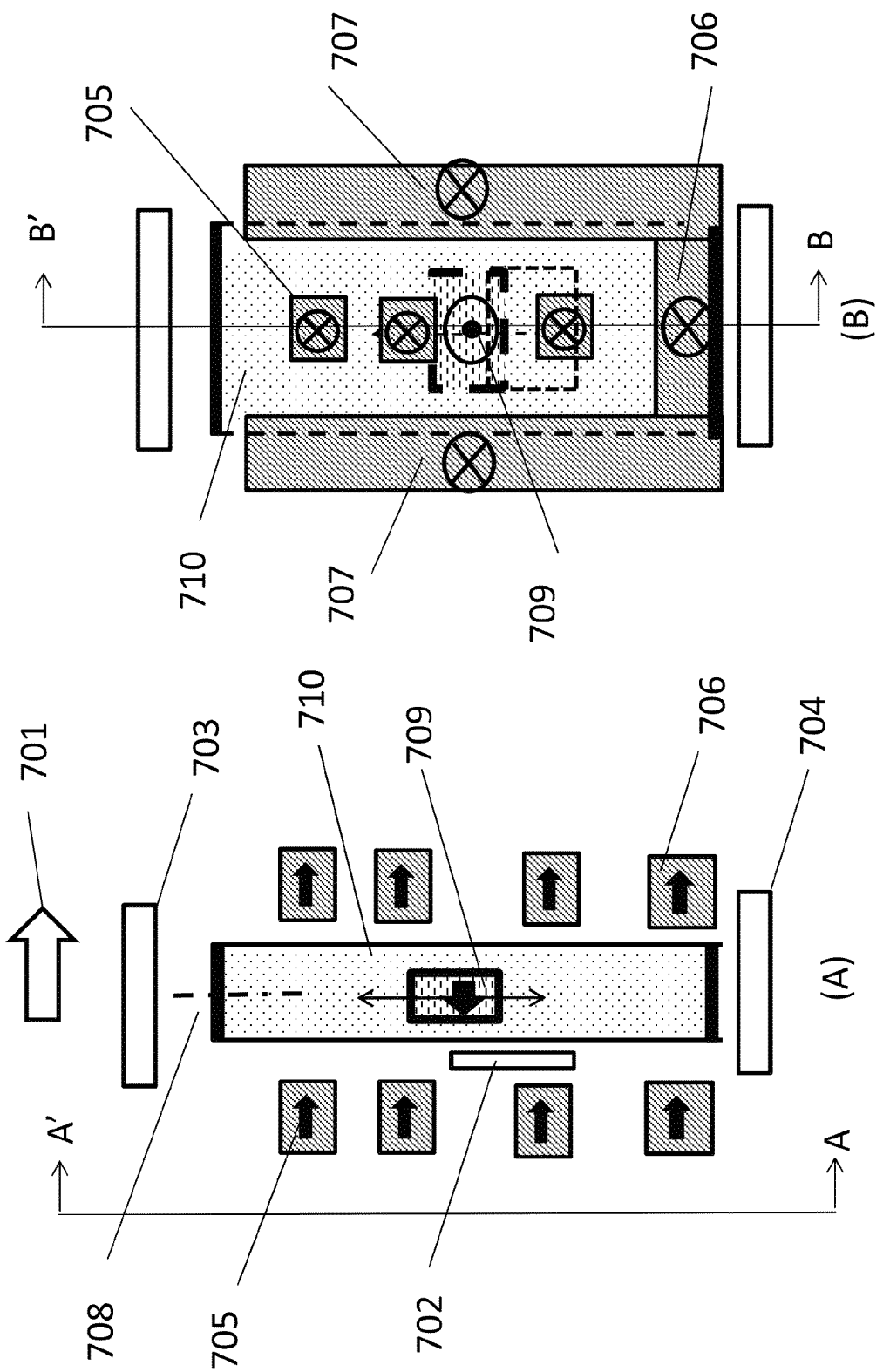
FIG. 7A-7B illustrate more detailed embodiment of the sensor design in FIG. 6.

FIG. 7A-7B show schematically more detailed design of FIG. 6 with the key components in order to better clarify the design principle. FIG. 7A illustrates the cross section view along B-B' line shown in FIG. 7B while FIG. 7B show the left to right view indicated by direction A-A' line shown in FIG. 7A. FIG. 7A is largely similar to what is shown in FIG. 6. Similar to FIG. 6, although three capacitive sensors 702, 703, and 704 are shown here, any one of them is enough for serving the purpose of detecting the position change of the floating magnet 709. The side array of magnets 705 along with bottom magnet 706 and side magnet 707 with the magnetization direction indicated by arrow and cross-in circle, respectively, shown in both FIGS. 7A and 7B, establish a sophisticated magnetic levitation mechanism for floating magnet 709, whose magnetization direction is opposed to that in the magnets outside the hollow tube 710. The centerline 708 of the hollow tube 710 is perpendicular to the magnetization directions of all magnets 705, 706, 707 and 709. The combination of magnets 705, 706 and 707 pushes the floating magnet 709 away from the inner walls, except the top wall, of the hollow tube 710 to ensure smooth movement with little friction.

For people with MEMS fabrication experience, particularly those skilled in the art of wafer fabrication, it is straight forward to make such as device with one capacitive sensor 702 with the feature/layer growth direction indicated by arrow 701. Alternative approach for layer growth direction can be used as well for the benefit for relatively easier to make sensor device 703 and 704.

Figure 8:
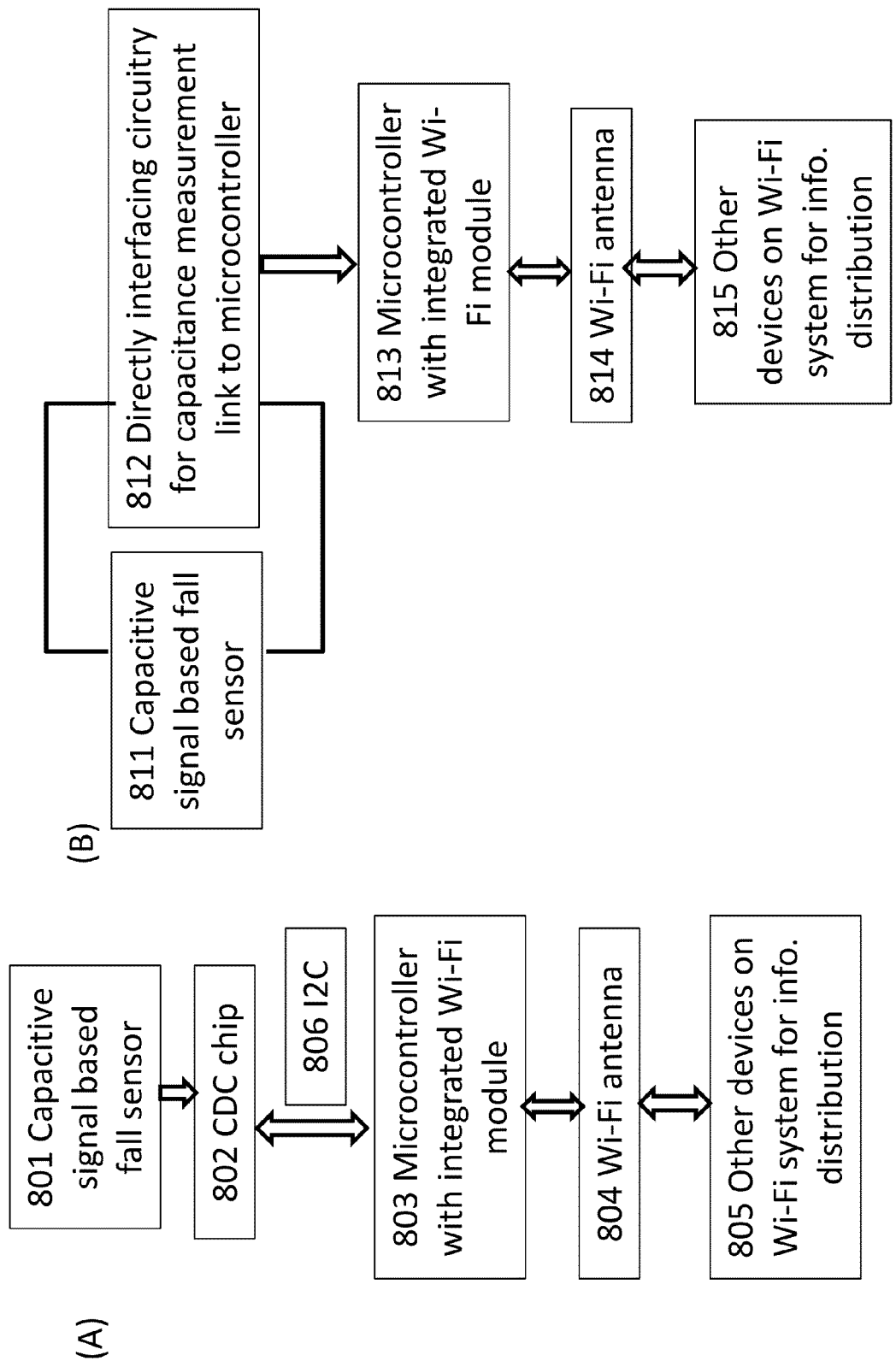
FIG. 8A-8B illustrate the block diagrams for the embodiments of fall sensor system with Wi-Fi enabled as a standalone device. (A) CDC-Microcontroller interface with built-in Wi-Fi, (B) directly interfacing connection to Microcontroller with built-in Wi-Fi.

FIG. 8A-8B show the block diagrams for one of the embodiments of fall sensor system with Wi-Fi enabled as standalone device or system. FIG. 8A shows a fall sensor system, which uses capacitance-digital-convertor (CDC) to mediate sensor and microcontroller with a built-in Wi-Fi module. In the figure, the signal obtained by sensor 801, i.e., the capacitance shown in FIGS. 3A and 3B, is converted to the digital number by the capacitance-digital-convertor (CDC) 802, and input, via Inter-Integrated Circuit (I2C) 806, to a microcontroller with integrated WI-FI module 803. Whether a real fall happens will be detected by analyzing the input data in the microcontroller 803. Once a real fall event is detected, the microcontroller 803 will send out the information such as SOS through the built-in Wi-Fi module's antenna 804 to other devices 805 within the same Wi-Fi system. By doing so, the emergency contact persons can be immediately informed by other devices 805 within the same Wi-Fi system, and the host can quickly get proper and effective helps from other persons.

FIG. 8B shows a fall sensor system with directly interfacing sensor to a microcontroller with built-in Wi-Fi module. The capacitive signal obtained by fall sensor 811 is integrated into a purposed design circuitry 812, which is directly connected to the microcontroller 813 through particularly designed I/O pins. The microcontroller 813 links with other devices on the same Wi-Fi network through Wi-Fi antenna 814. Whether a real fall happens will be detected by analyzing the capacitive signal in the microcontroller 813. Once a real fall happens, the system will inform the emergency contact persons for help immediately through the Wi-Fi system. The system shown in FIG. 8B is simpler and cheaper than that shown in FIG. 8A provided the initial capacitance value and its change between pre-fall and post-fall are bigger enough. For the sensor designs shown in this invention, these conditions are relatively easy to fulfill.

Figure 9:
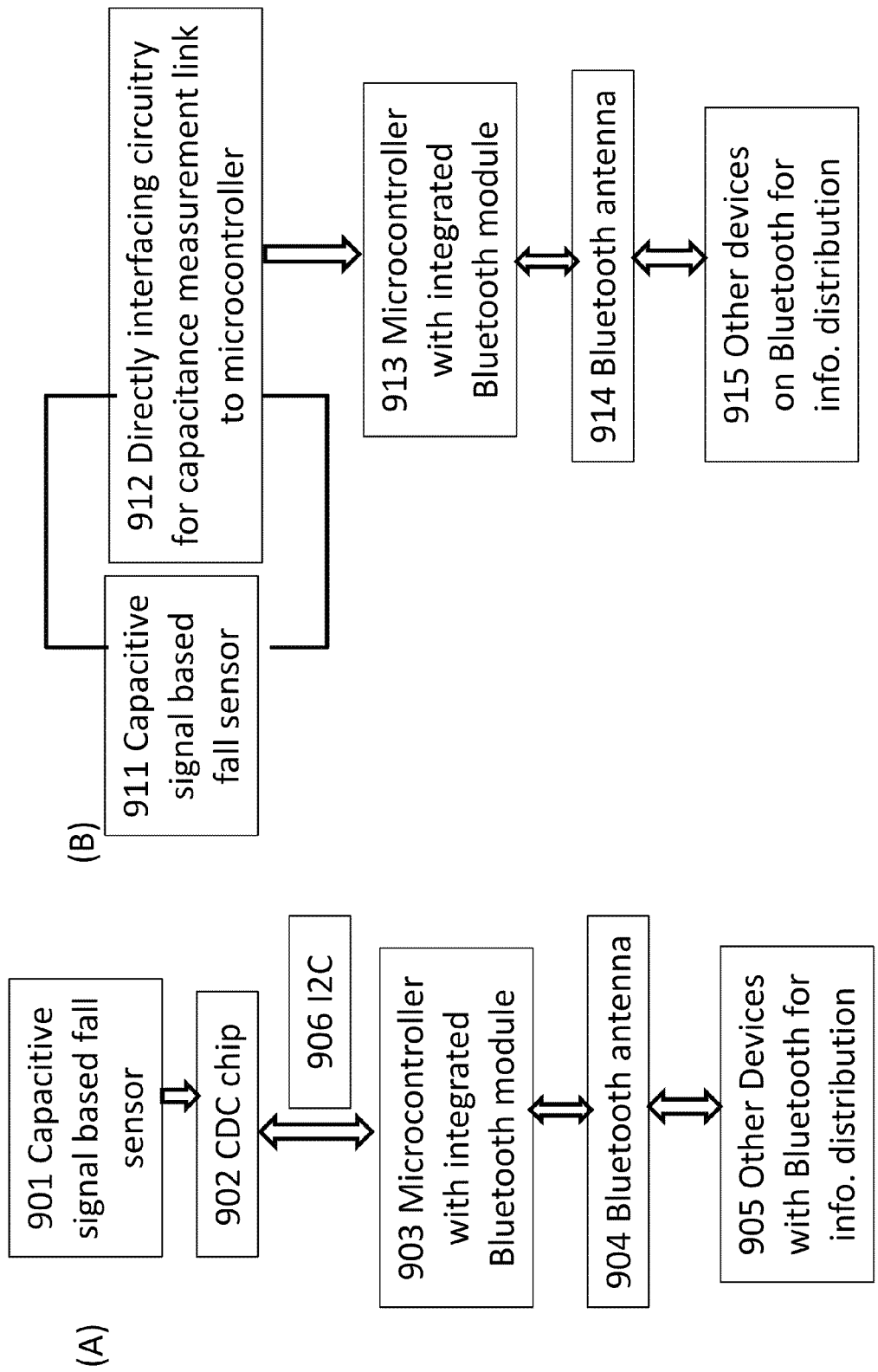
FIG. 9A-9B illustrate the block diagrams for the embodiments of fall sensor system with Bluetooth enabled as a standalone device. (A) CDC-microcontroller interface with built-in Bluetooth, (B) directly interfacing connection to microcontroller with built-in Bluetooth.

FIG. 9A-9B show the block diagrams for one of the embodiments of fall sensor system with Bluetooth wireless communication enabled as a standalone device or system. FIG. 9A shows a fall sensor system, which uses capacitance-digital-convertor (CDC) to mediate sensor and microcontroller with a built-in Bluetooth module. Same as that addressed in FIG. 8A, the signal obtained by sensor 901, i.e., the capacitance, is converted to the digital number by the capacitance-digital-convertor (CDC) 902, and input, via Inter-Integrated Circuit (I2C) 906, to a microcontroller with integrated Bluetooth module 903. Whether a real fall happens will be detected by analyzing the input data in the microcontroller 903. Once a real fall event is detected, the microcontroller 903 will send out the information such as SOS through the built-in Bluetooth module's antenna 904 to other devices 905 within the same Bluetooth, the emergency contact persons will be immediately informed by other Bluetooth devices 905, and the host can get quick and proper helps.

FIG. 9B shows a fall sensor system with directly interfacing sensor to a microcontroller with built-in Bluetooth module. Same as that addressed in FIG. 8B, the capacitive signal obtained by fall sensor 911 is integrated into a purposed design circuitry 912, which is directly connected to microcontroller 913 through particularly designed I/O pins. The microcontroller 913 links with other devices through built-in Bluetooth's antenna 914 to communicate with outside. Once a real fall is detected by analyzing the capacitive signal in the microcontroller 913, the emergency contact persons will be immediately informed to help the host quickly and properly by other devices 915 through Bluetooth network. The system in FIG. 9B is simpler and cheaper than that in FIG. 9A provided the initial capacitance value and its change between pre-fall and post-fall is bigger enough. For the sensor designs shown in this invention, these conditions are relatively easy to fulfill.

The communication schemes for the fall detection system shown both in FIGS. 8A-8B and in FIGS. 9A-9B can be used to build up other sensor system, such as individual health smart system to routinely monitor people's pulse, body temperature, oxygen content in blood, blood pressure, etc., and prevent from fatal health conditions by early treatment.

Figure 10:
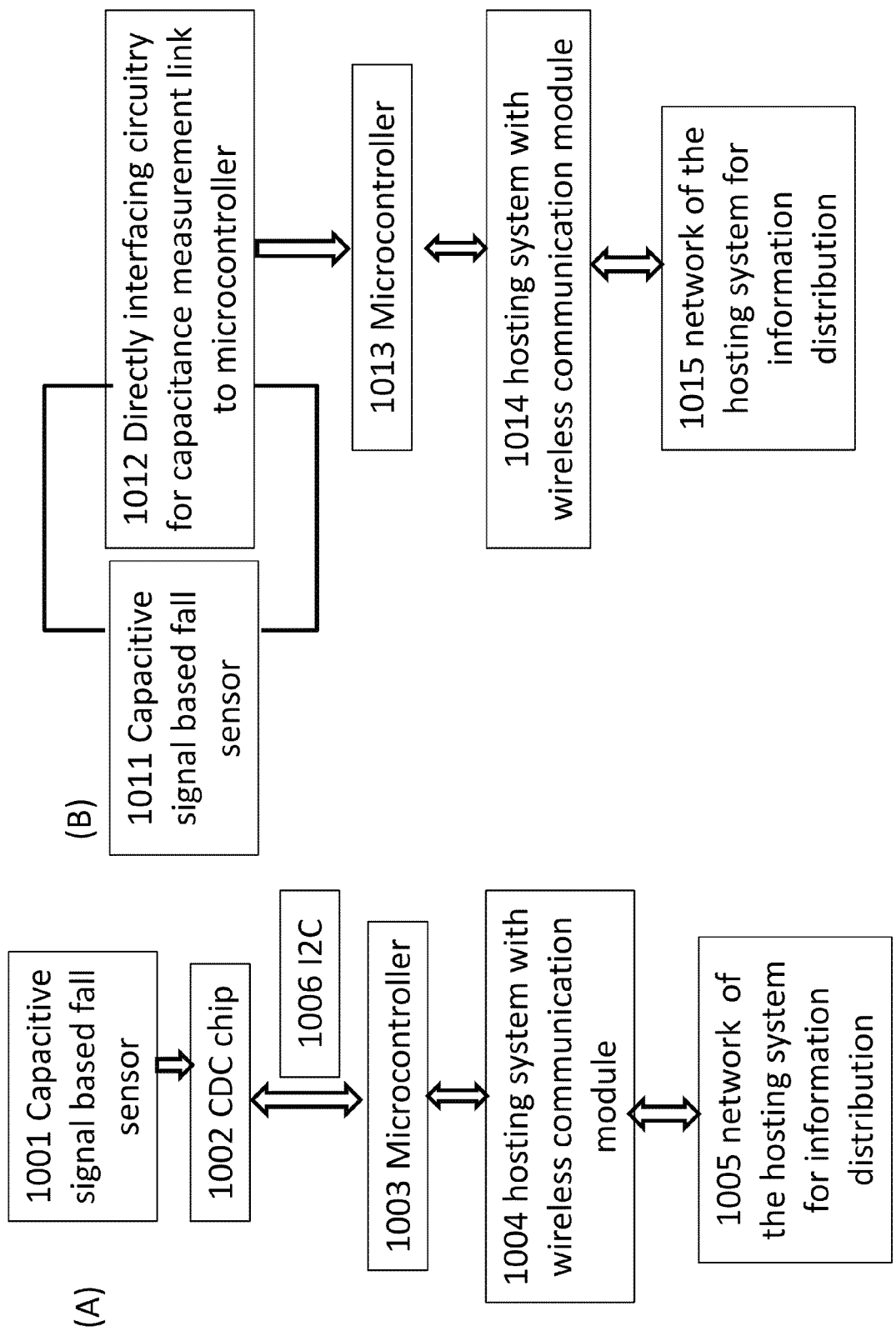
FIG. 10A-10B illustrate the block diagrams for the embodiments of fall sensor system built as integrated part of the component for portable or wearable devices. (A) CDC mediated system; (B) directly interfacing connection to microcontroller.

FIG. 10A-10B illustrate the block diagrams for the embodiments of fall sensor system built as integrated part of the component for portable or wearable devices. FIG. 10A shows an integrated fall detection system using CDC for capacitance sensing. In this case, the signal from capacitive signal based fall sensor 1001 is converted to digital information by the CDC 1002, and analyzed by the microcontroller 1003. The microcontroller 1003 uses the predetermined methodology to detect whether a fall event happens. Inter-Integrated Circuit (I2C) 1006 is used as a bridge to communicate between the CDC 1002 and the microcontroller 1003. Once a fall event is detected by the microcontroller 1003, the emergency information will be distributed by hosting system 1004 to the parties who connect with the hosting system through the network 1005, and proper actions will be taken quickly by the parties who concern.

FIG. 10B shows an integrated fall detection system using directly interfacing connection to microcontroller for signal detection. The capacitive signal based fall sensor 1011 is integrated into a purposed design circuitry 1012 that directly connects with the microcontroller 1013 through particularly designed I/O pins. Same as that in FIG. 10A, the microcontroller 1013 communicates with outside the hosting system 1014 and the network 1015 to distribute the information to wide audience.

Figure 11:
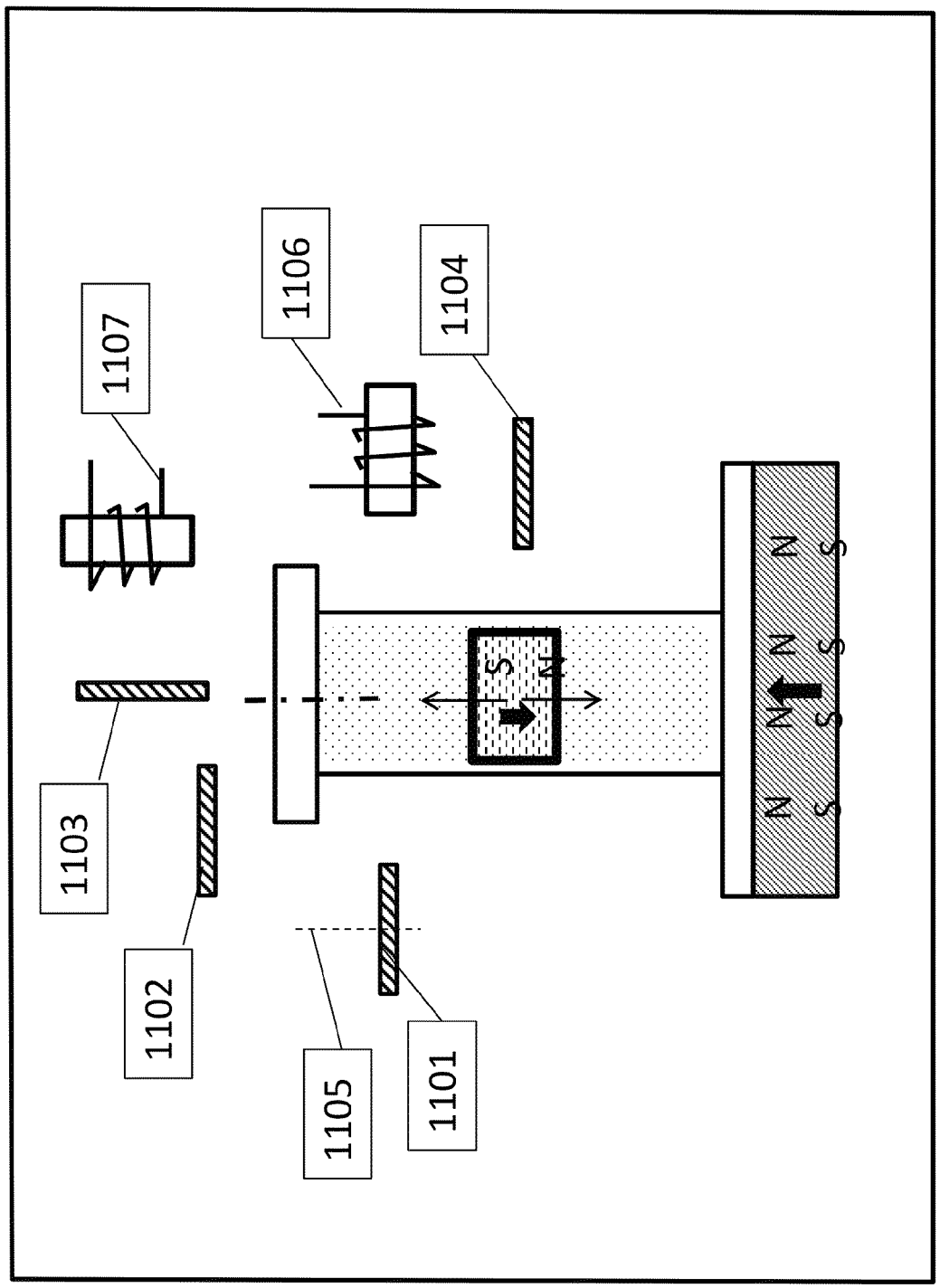
FIG. 11 illustrates another embodiment similar to what is shown in FIG. 1 but the device uses either the solid magnetic field sensor or magnetic flux pickup coil to detect the location of the floating object.

FIG. 11 illustrates another embodiment similar to what is shown in FIG. 1 but the device uses either the solid magnetic field sensor or magnetic flux pickup coil to detect the location of the floating object. In FIG. 11, there are four solid magnetic field sensors 1101, 1102, 1103, 1104, and two magnetic pickup coil sensors 1106 and 1107. The dot-line 1105 represents the solid magnetic field sensor growth direction. The different arrangements of the sensors shown in FIG. 11 are demonstrated that the exact design could be varied according to the sensitivity requirements and manufacturability. The solid magnetic field sensor can be magnetoresistive sensor based on anisotropic magnetoresistive (AMR) effect, giant magnetoresistive (GMR) effect, tunneling magnetoresistive (TMR) effect, semiconductor field sensor based on such as Hall Effect, or magneto-impedance sensor (MIS).

Figure 12A:
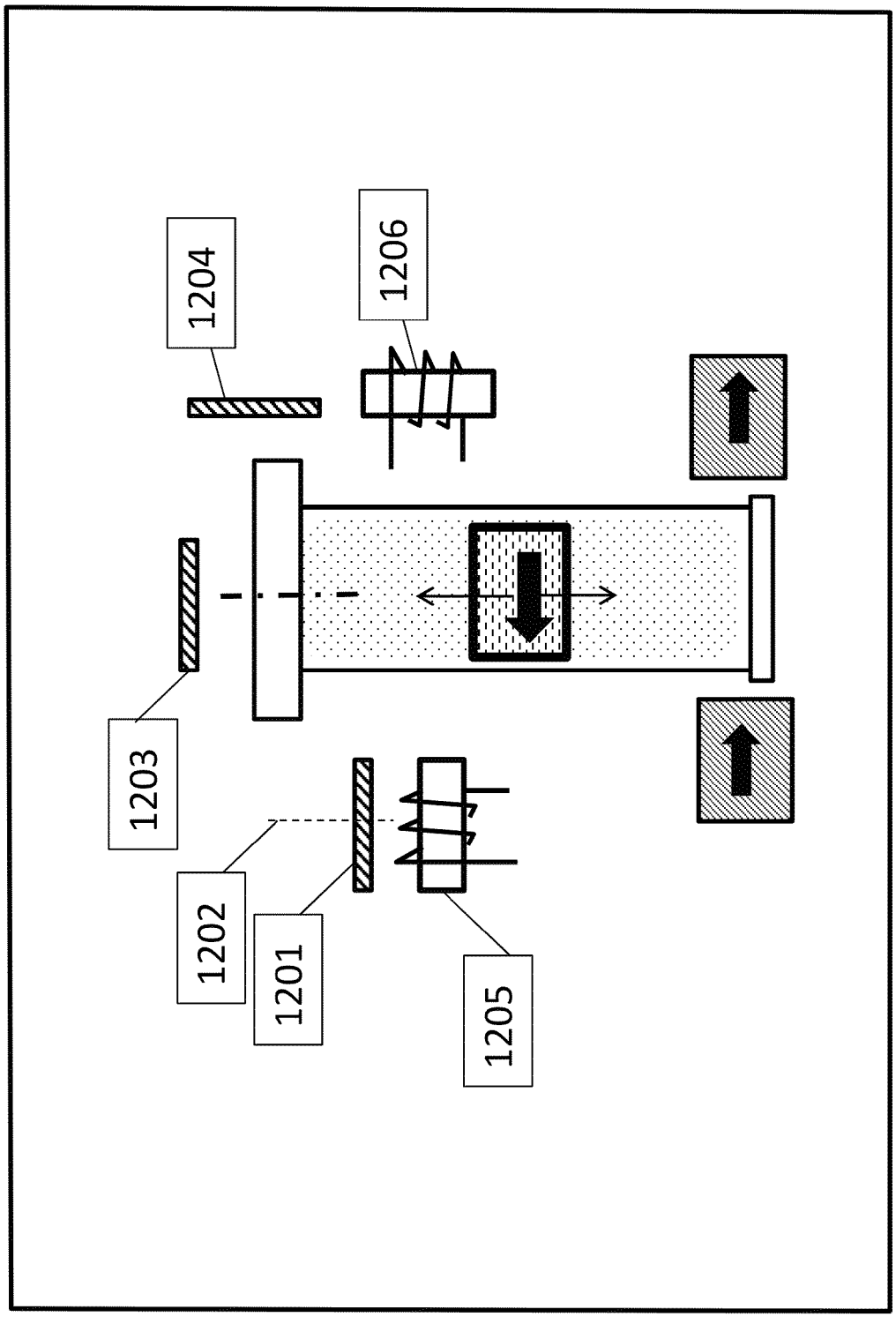
FIG. 12A-12B illustrate another embodiments similar to what are shown in FIG. 5 and FIG. 6, respectively, but the device uses either the solid magnetic field sensor or magnetic flux pickup coil to detect the location of the floating object.
Figure 12B:
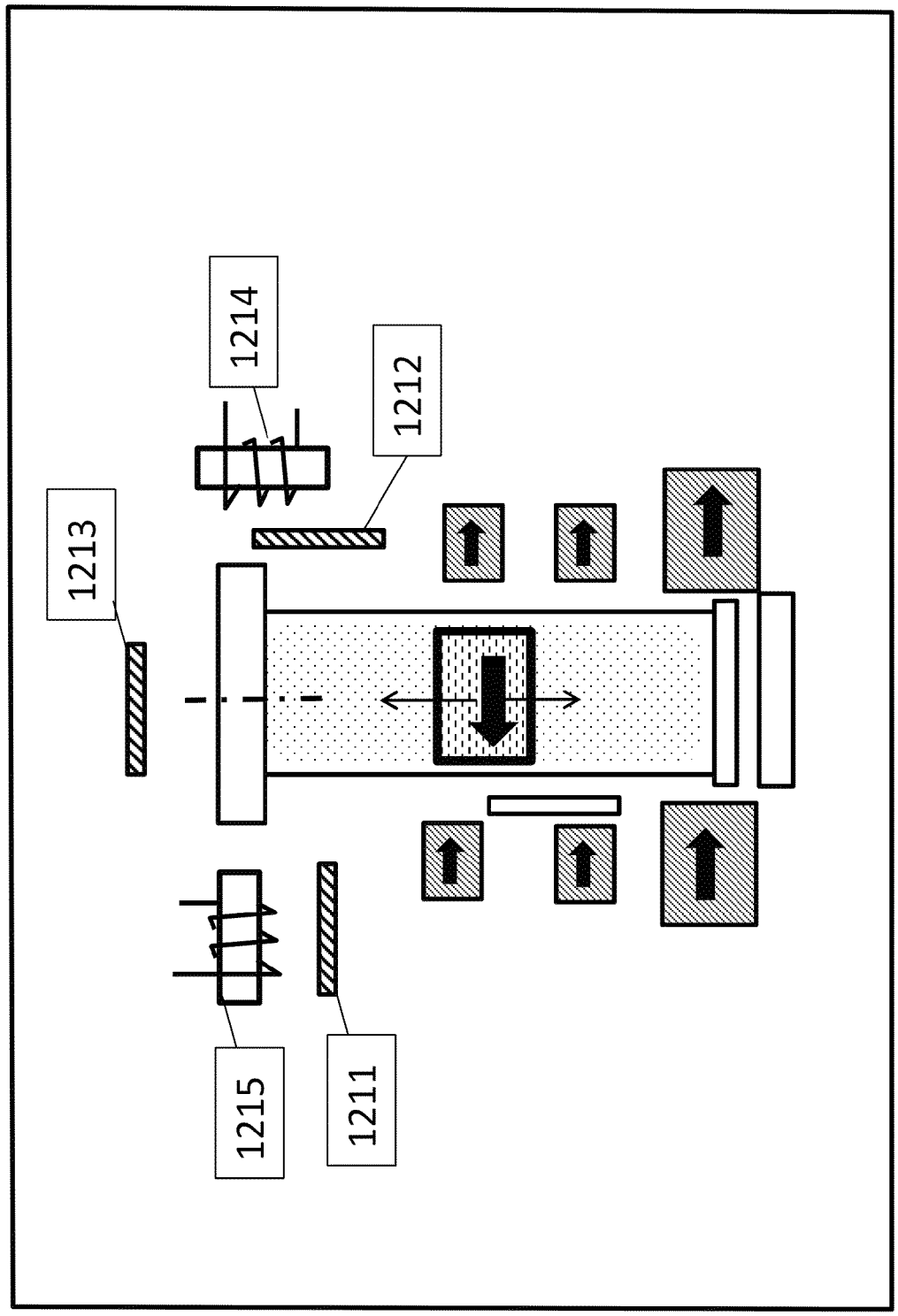

FIG. 12A-12B illustrate another embodiments similar to what are shown in FIG. 5 and FIG. 6, respectively, but the device uses either the solid magnetic field sensor or magnetic flux pickup coil to detect the location of the floating object. In FIG. 12A, there are three solid magnetic field sensors 1201, 1203, 1204, and two magnetic pickup coil sensors 1205 and 1206. The dot-line 1202 represents the solid magnetic field sensor growth direction. In FIG. 12B, there are three solid magnetic field sensors 1211, 1212, 1213, and two magnetic pickup coil sensors 1214 and 1215. The different arrangements of the sensors shown in FIG. 12A and FIG. 12B are demonstrated that the exact design could be varied according to the sensitivity requirements and manufacturability. The solid magnetic field sensor can be magnetoresistive sensor based on anisotropic magnetoresistive (AMR) effect, giant magnetoresistive (GMR) effect, tunneling magnetoresistive (TMR) effect, semiconductor field sensor based on such Hall Effect, or magneto-impedance sensor (MIS).

In a more elegant or power saving design, a reed sensor/or reed switch can be integrated into above proposed sensors.

FIG. 13A-13B show schematically the mechanism on how to integrate a reed sensor/or reed switch into above proposed sensors. The reed sensor/or reed switch comprises a movable part 1301, such as a cantilever, which can move along the direction indicated by the dual arrow 1302; a small ferromagnetic metallic contact pad 1303 at the end of the 1301; a big non-magnetic metallic contact pad 1304; the wire system connected to 1303 and 1304, whose ends are 1306 and 1307, respectively. The 1306 and 1307 also connect to the external ASIC circuit for sensor output analysis and responses. The elastic restoring force of movable part 1301 is used to turn off red sensor/or reed switch circuit. At normal standup status, the floating hard magnet 1305 is at its equilibrium position inside the hollow tube 1308, and the reed sensor/or reed switch circuit is off to save power since the magnetic attractive force between 1305 and 1303 is too week (magnetic force is proportional to $1/r^3$ while r is the distance between two magnetic objectives) to overcome the elastic restoring force of movable part 1301. The magnetic attractive force between 1305 and 1303 increases dramatically when the floating hard magnet 1305 moves toward to 1303 inside the hollow tube 1308 due to the host's activities such as jumping, skiing, walking, or falling, etc. The magnetic attractive force between 1305 and 1303 will be large enough to blend the movable part 1301, and finally turn on the reed sensor/or reed switch circuit when the floating hard magnet 1305 moves into the pre-determined distance range. The mass of the floating hard magnet 1305 is much larger than that of movable part 1301. Even though the magnetic attractive force is large enough to turn on the reed sensor/or reed switch circuit, it is still too week to have little impact on the movement of the floating hard magnet 1305 inside the hollow tube 1308.

The reed sensor/or reed switch will generates "on/off" binary signal. The microcontroller shown in FIG. 8, FIG. 9 and FIG. 10 will analyze the binary signal to determine the host's movements. The host's sports activities, such as jumping, skiing, walking, etc., will generate high frequency "on/off" signal, and the microcontroller will switch the system as smart exercise monitor instead of fall detection. Only when the host is falling down shown in FIG. 13B, the reed sensor/or reed switch will generate a "on" signal longer than a pre-set time, such as 15 seconds, to trigger the microcontroller to send out a fall alarm, which will be discussed in more details in the following context.

Figure 13:
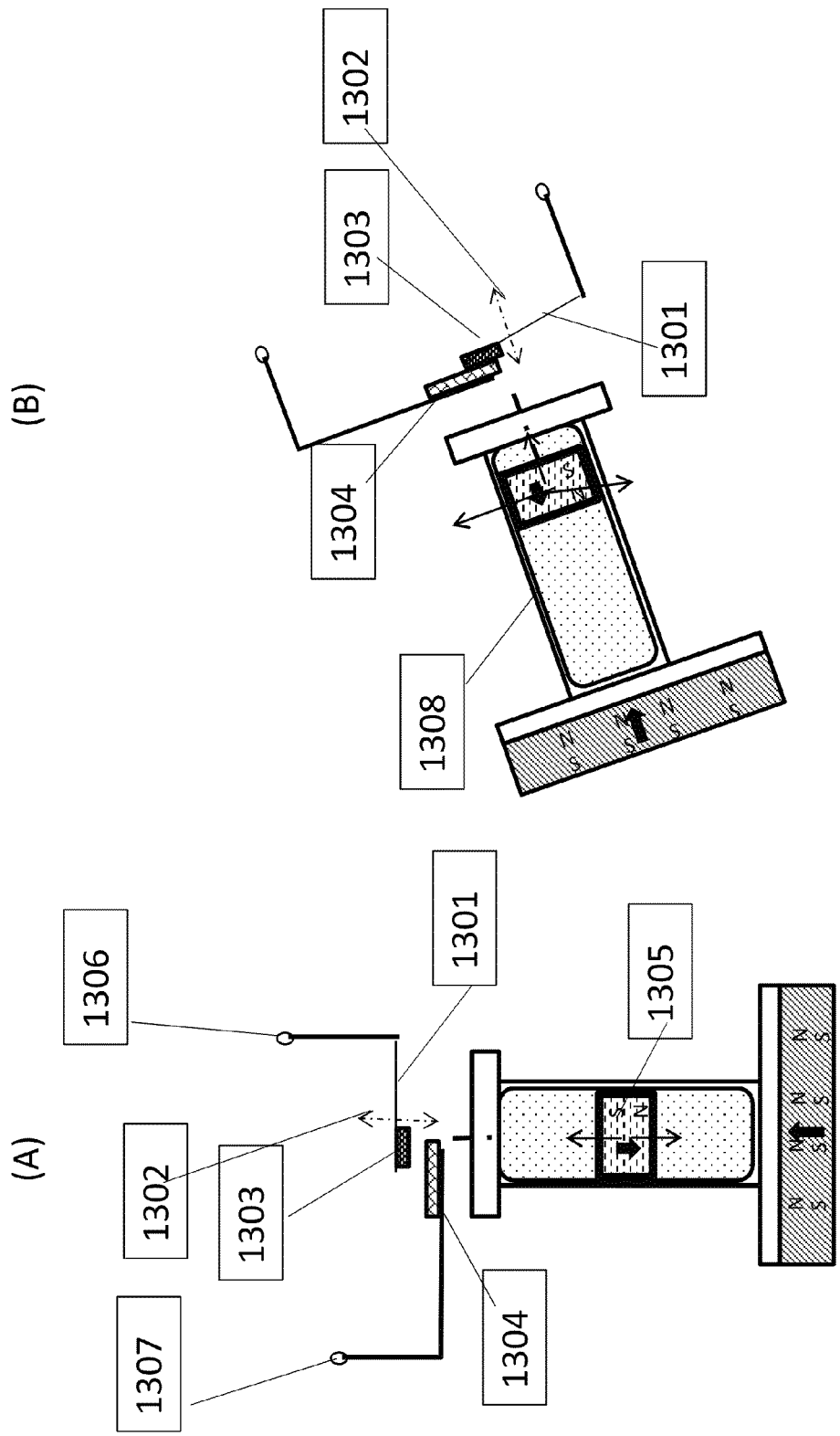
FIG. 13A-13B illustrate schematically the mechanism on how to integrate a reed sensor/switch into the proposed fall sensors.
Figure 14:
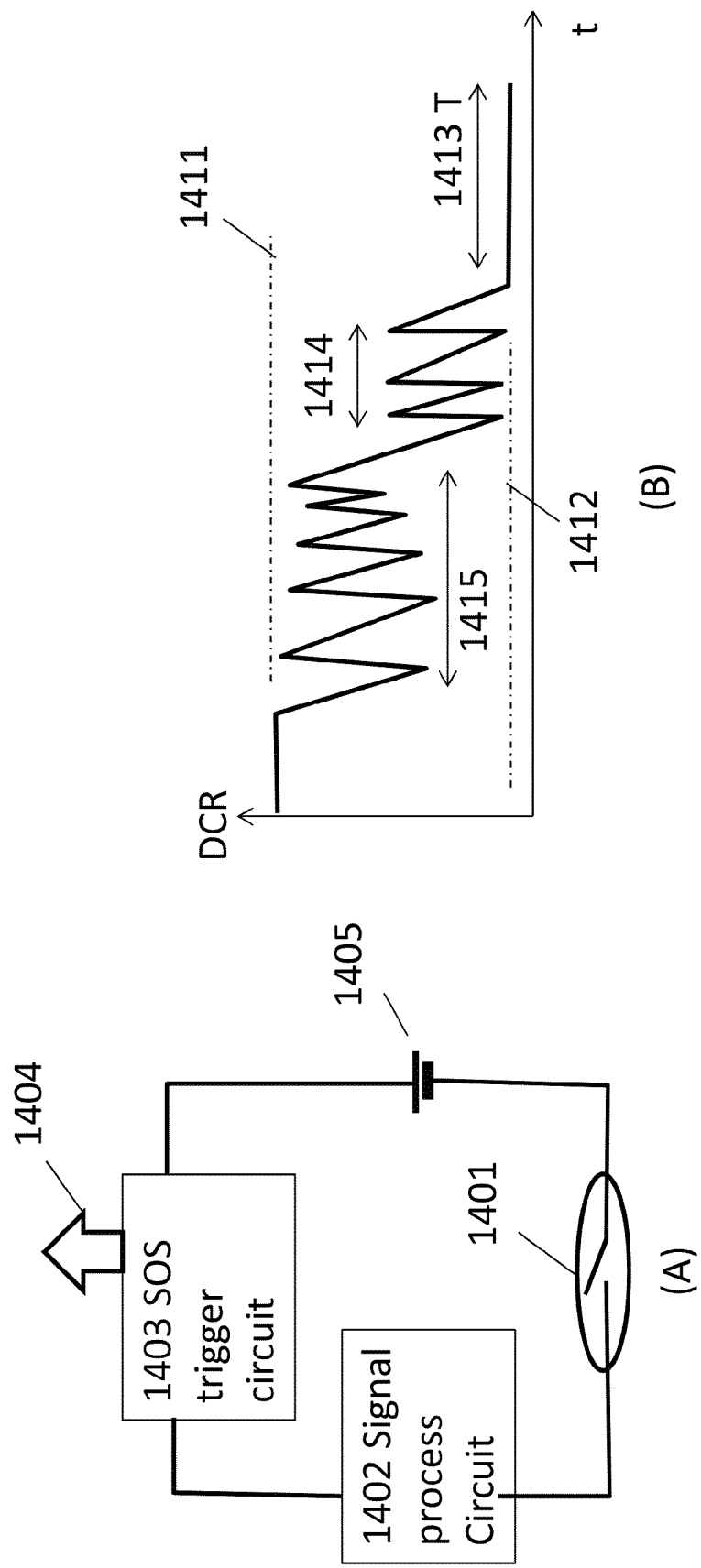
FIG. 14A-14B show how the reed sensor system works as fall sensor. (A) the simple circuit diagram of the external detection ASIC; (B) an exemplary signal.

FIG. 14A-14B show how the reed sensor system works as fall sensor. FIG. 14A shows a simple circuit diagram of the external detection ASIC for sensor system based on reed sensor/or reed switch shown in FIG. 13. The ASIC comprises a reed sensor/or reed switch 1401, a power resource 1405, a signal process circuit 1402 to obtain the duration/frequency of "on/off" signal, a SOS trigger circuit 1403 linked to external system 1404, which can further distribute the fall alarm to wide audience. The biggest advantage of such a design is that the whole circuitry is working at passive mode. No power supply is needed when the reed sensor/or reed switch is off. As such, it is one of the most power saving and preferred design for portable and wearable devices and applications. The SOS circuit will send out the fall alarm only when the reed sensor/or reed switch 1401 keeps on longer than the pre-set time, such as 15 seconds.

FIG. 14B shows an exemplary signal. The Y and X axes correspond to the dynamic contact resistance (DCR) of the reed sensor/or reed switch and time. The two levels of DCR 1411 and 1412 represent the open and close statuses of the reed sensor/or reed switch 1401 in FIG. 14A, respectively. Large oscillating signal close to open status 1411 in the time duration 1415 represents the active movement of the host against falling, which leads to short close-and-open of the reed sensor/or reed switch 1401 in FIG. 14A. Large signal variation but close to the close status 1412 in the time duration 1414 indicates the falling process. The signal in the time duration 1413 that is at close status level of 1412 and has a duration time T longer than the pre-set time confirms that a real fall event is indeed detected. Under such circumstance, the signal in the time duration 1413 will trigger the 1403 in FIG. 14A to create a fall alarm and send out a SOS signal for help.

The DCR of the reed sensor/or reed switch has a closely correlated relationship with the tilting angle of the sensor shown in FIG. 13. After calibration, the DCR can be used to measure the tilting angle of object, on which the sensor is fixed with long axis of sensor parallel to local gravity.

What is claimed is:

1. A fall detection system, whose orientation with respect to its host body is fixed when it is being used, comprising:
    at least one sensor subsystem to detect the orientation change of said host body with respect to the local gravity direction;
    said sensor subsystem comprises:
    a floating object and detects fall by sensing the displacement of said floating object from its equilibrium position, where its gravity is well balanced by interaction force provided by other component(s) within said sensor subsystem before fall;
    an elongated hollow tube with its longer axis purposely orientated along the local gravity direction when said host body stands straight on a flat surface normal to local gravity direction;
    a floating structure containing hard magnet inside said hollow tube, which has predetermined smaller dimensions than said hollow tube and is capable of moving smoothly inside said hollow tube;
    at least one sensing device, which can detect the position of said floating structure containing hard magnet within said hollow tube;
    at least one permanent magnet, whose magnetization is opposite to the magnetization of the hard magnet within said floating structure and provide magnetic levitation to said floating structure containing hard magnet.

2. The system of claim 1, wherein said fall detection system is built either as a standalone wearable or portable device or as an integrated functional component in a smart phone, or tablet, or other wearable or portable device.

3. The system of claim 2, wherein said standalone wearable or portable system is an electronic belt, or an electronic necklace, or an electronic earring, or electronic brooch, or electronic tie clip, or electronic lapel pin, or an electronic tag, or any electronic wearable/portable fashion article.

4. The system of claim 1, wherein the magnetization of said hard magnet within said floating structure is aligned close to either parallel or normal to the longer axis of said elongated hollow tube.

5. The system of claim 1, wherein said sensing device is a capacitive sensor, therefore the system is a capacitive sensor based fall detection system.

6. The system of claim 5, wherein said capacitive sensor locates on top, or on bottom, or on the side of said hollow tube, or on anywhere closely around said hollow tube.

7. The system of claim 5, wherein said capacitive sensor is either a capacitive button sensor or a capacitive sensor with pair of electrodes outside said elongated hollow tube.

8. The system of claim 5, wherein said capacitive sensor based fall detection system uses an abrupt change of the capacitance value from its pre-known normal level before fall to the pre-set post-fall level as a necessary condition for fall happening.

9. The system of claim 8, wherein said capacitive sensor based fall detection system confirms whether the fall event really happens according to the fact that the output capacitance value stays at the pre-set post-fall level longer than a pre-determinate time duration.

10. The system of claim 8, wherein said abrupt change of the capacitance value is better detected by using differential signal of the raw capacitive value with pre-optimized smoothening and peak detect algorithm.

11. The system of claim 5, wherein said capacitive sensor is linked to capacitance-digital convertor chip, which communicates, via Inter-Integrated Circuit (I2C), to a microcontroller with an integrated wireless communication module used for further information distribution.

12. The system of claim 5, wherein said capacitive sensor is part of directly interfacing circuitry for capacitance measurement linked to microcontroller with an integrated wireless communication module for wide information distribution.

13. The system of claim 1, wherein said sensing device is either a magnetic field induction pickup coil, or a magnetoresistive (MR) sensor, or a Hall effect sensor, or a magnetoimpedance (MI) sensor, or magnetoelastic (ME) sensor.

14. The system of claim 13, wherein said magnetoresistive (MR) sensor is based on either anisotropic magnetoresistive (AMR), or giant magnetoresistive sensor (GMR), or tunneling magnetoresistive (TMR) phenomena.

15. The system of claim 13, wherein either said field induction pickup coil, or said magnetoresistive (MR) sensor, or said Hall Effect sensor, or said magneto-impedance (MI) sensor, or said magnetoelastic (ME) sensor is designed to place on anywhere around said hollow tube according to predetermine sensitivity requirements and manufacturability.

16. The system of claim 1, wherein said sensing device comprises fall detection application-specific integrated circuit (ASIC) linked to either a reed sensor/or reed switch, or Microelectromechanical systems (MEMES) based reed sensor/or reed switch, which turns on or off the circuit based on the position of said floating structure containing hard magnet within said hollow tube.

17. The system of claim 16, wherein said application-specific integrated circuit (ASIC), working in a passive mode at normal circumstance before fall and being activated by said reed sensor/or reed switch after the fall even is detected to send out the fall alarm, comprises a signal analysis circuit, which acts as arbitrator to confirm whether the fall happens by comparing the time duration of the close of said reed sensor/or reed switch with the pre-determinate threshold value.

18. The system of claim 16, wherein the dynamic contact resistance of said reed sensor/or reed switch has a close relation with the tilt of said sensor subsystem, and is used to measure the tilting angle of its host body with respect to the direction of local gravity.

* * * * *